US011834680B2

(12) United States Patent
Sabaawy

(10) Patent No.: US 11,834,680 B2
(45) Date of Patent: Dec. 5, 2023

(54) SINGLE KIDNEY CELL-DERIVED ORGANOIDS

(71) Applicant: Rutgers, The State University of New Jersey, New Brunswick, NJ (US)

(72) Inventor: Hatem Sabaawy, Neshanic Station, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 857 days.

(21) Appl. No.: 16/626,053

(22) PCT Filed: Jun. 28, 2018

(86) PCT No.: PCT/US2018/040022
§ 371 (c)(1),
(2) Date: Dec. 23, 2019

(87) PCT Pub. No.: WO2019/006127
PCT Pub. Date: Jan. 3, 2019

(65) Prior Publication Data
US 2021/0147809 A1 May 20, 2021

Related U.S. Application Data

(60) Provisional application No. 62/526,059, filed on Jun. 28, 2017.

(51) Int. Cl.
*A61K 35/22* (2015.01)
*C12N 5/071* (2010.01)
*A01K 67/027* (2006.01)
*A61K 49/00* (2006.01)
*C12N 5/00* (2006.01)
*G01N 33/50* (2006.01)

(52) U.S. Cl.
CPC ........ *C12N 5/0686* (2013.01); *A01K 67/0271* (2013.01); *A61K 35/22* (2013.01); *A61K 49/0008* (2013.01); *C12N 5/0062* (2013.01); *G01N 33/5011* (2013.01); *G01N 33/5088* (2013.01); *A01K 2207/12* (2013.01); *A01K 2207/15* (2013.01); *A01K 2227/105* (2013.01); *A01K 2267/0331* (2013.01); *C12N 2500/38* (2013.01); *C12N 2501/105* (2013.01); *C12N 2501/11* (2013.01); *C12N 2501/115* (2013.01); *C12N 2501/165* (2013.01); *C12N 2501/33* (2013.01); *C12N 2501/39* (2013.01); *C12N 2501/415* (2013.01); *C12N 2501/727* (2013.01); *C12N 2501/998* (2013.01); *C12N 2501/999* (2013.01); *C12N 2513/00* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,529,920 | A | 6/1996 | Cole et al. |
| 5,712,163 | A | 1/1998 | Parenteau et al. |
| 2005/0054102 | A1 | 3/2005 | Wobus et al. |
| 2005/0107294 | A1 | 5/2005 | Acosta et al. |
| 2005/0233446 | A1 | 10/2005 | Parsons et al. |
| 2010/0233240 | A1 | 9/2010 | Koizumi et al. |
| 2012/0230966 | A1 | 9/2012 | Crawford et al. |
| 2014/0289877 | A1 | 9/2014 | Taniguchi et al. |
| 2014/0302491 | A1 | 10/2014 | Nadauld et al. |
| 2016/0101133 | A1 | 4/2016 | Basu et al. |
| 2016/0237409 | A1 | 8/2016 | Little et al. |

FOREIGN PATENT DOCUMENTS

| | | | |
|---|---|---|---|
| WO | 1993002188 | A1 | 2/1993 |
| WO | 2001007056 | A1 | 2/2001 |
| WO | WO 15/196012 | * | 12/2015 |
| WO | WO 16/094948 | * | 6/2016 |

OTHER PUBLICATIONS

Yin, Cell Stem Cell, 2016, 18: 25-38.*
Wilson et al., Front. Immunol., 2021, 11: 1-18.*
Kitamura et al., Stem Cells, 2015, 33: 774-784.*
Takasato et al., Nature Protocols, 2016, 11: 1581-1692.*
Qian et al., Int. J. Mol. Med., 2008, 22: 325-332.*
Tong et al., Modern Pathology, 2009, 22: 1218-1227.*
McCabe, et al: "Efficient Generation of Human Embryonic Stem Cell-Derived Corneal Endothelial Cells by Directed Differentiation", Plos One, Dec. 21, 2015, vol. 10, No. 12, pp. 1-24.

(Continued)

*Primary Examiner* — Ileana Popa
(74) *Attorney, Agent, or Firm* — FOX ROTHSCHILD LLP

(57) ABSTRACT

The present invention relates to organoids derived from a single cell, such as a kidney cancer cell, and methods and compositions relating to the production and use thereof, including cell culture medium for producing organoids and methods of personalized treatment for kidney cancer. The invention further provides a humanized mouse including a kidney organoid derived from a patient's kidney cell.

9 Claims, No Drawings

(56) References Cited

OTHER PUBLICATIONS

Lobo, et al: "Efficient Generation of Patient-Matched Malignant and Normal Primary Cell Cultures from Clear Cell Renal Cell Carcinoma Patients; Clinically Relevant Models for Research and Personalized Medicine", BMC Cancer, Jul. 16, 2016, vol. 16, No. 485, pp. 1-15.
Bartucci, et al: "Personalized Medicine Approaches in Prostate Cancer Employing Patient Derived 3D Organoids and Humanized Mice", Frontiers in Cell and Development Biology, Jun. 2016, vol. 4, No. 64, pp. 1-8.
Wang, et al: "Cultured Circulating Tumor Cells and their Derived Xenografts for Personalized Oncology", Asian Journal of Urology, Oct. 1, 2016, vol. 3, No. 4, pp. 240-253.
Patrizii, et al: "Utility of Glioblastoma Patient-Drived Orthotopic Xenogafts in Drug Discovery and Personalized Therapy", Frontiers in Oncology, Feb. 12, 2018, vol. 8, No. 23, pp. 1-9.

\* cited by examiner

SINGLE KIDNEY CELL-DERIVED ORGANOIDS

CROSS-REFERENCE TO RELATED APPLICATION

This application claims the benefit of U.S. Provisional Application No. 62/526,059 filed Jun. 28, 2017, the disclosure of which is incorporated herein by reference in its entirety.

BACKGROUND OF THE INVENTION

The inability to propagate primary tissues represents a major hurdle to understanding the mechanisms of regeneration and the balance of differentiated cells versus stem cells in adult organisms. A need exists to better understand primary human pathological disorders such as injury repair and tumor development. For cancer studies, current cancer models do not adequately represent the molecular and cellular diversity of human cancers. Existing human cancer cell lines lack defined and detailed information regarding the clinical presentation of the cancer and have inherent limitations for deciphering the mechanisms of therapy resistance. For injury repair, there is a lack of understanding of the mechanisms of regeneration and shortage of tissue and organs for transplantation. Therefore, novel methods to maintain primary tissues for cancer, new drug discovery approaches to treat cancer and regenerative medicine indications are needed.

Maintaining the balance between normal differentiated cells and progenitor or stem cells is complex. Adult stem cells provide regeneration of different tissues, organs, or neoplastic growth through responding to cues regulating the balance between cell proliferation, cell differentiation, and cell survival, with the later including balanced control of cell apoptosis, necrosis, senescence and autophagy. Epigenetic changes, which are independent of the genetic instructions but heritable at each cell division, can be the driving force towards initiation or progression of diseases. Tissue stem cells are heterogeneous in their ability to proliferate, self-renew, and differentiate and they can reversibly switch between different subtypes under stress conditions. Tissue stem cells house multiple subtypes with propensities towards multi-lineage differentiation. Hematopoietic stem cells (HSCs), for example, can reversibly acquire three proliferative states: a dormant state in which the cells are in the quiescent stage of the cell cycle, a homeostatic state in which the cells are occasionally cycling to maintain tissue differentiation, and an activated state in which the cells are cycling continuously. The growth and regeneration of many adult stem cell pools are tightly controlled by these genetic and/or epigenetic responses to regulatory signals from growth factors and cytokines secreted through niche interactions and stromal feedback signals.

Chronic kidney disease (CKD) affects 9-14% of the U.S. adult population and all six regions of the world. Loss of function of nephrons and the development of tubule-interstitial fibrosis contribute to the progression of CKD, which impairs the regulation of fluid—electrolyte and acid—base balance, as well as the excretion of metabolic waste products with accumulation of uremic toxins. While adult kidneys possess an intrinsic capacity to self-repair following injury, the process of nephrogenesis, the formation of new nephrons, is thought to be limited to the period of embryonic development in humans. Regenerative medicine applications for kidney failure, kidney cancer and organ replacement therapy are needed.

SUMMARY OF THE INVENTION

In one embodiment, the present invention provides a method of making an organoid from a mammalian kidney tissue in vitro comprising: isolating cells from a mammalian kidney tissue to provide isolated cells; culturing the isolated cells in a differentiation medium for a time sufficient to enrich for stem cells and induce differentiation; and amplifying the cells by culturing in an extracellular matrix in an organoid medium for a time sufficient to produce organoids.

In another embodiment, the invention provides an in vitro kidney organoid comprising epithelial cells (e.g., duct and nephron epithelial cells).

In one embodiment, the in vitro kidney organoid is derived from a single epithelial cell of a kidney tissue.

In another embodiment, the invention provides an in vitro kidney organoid derived from primary kidney normal tissue, wherein the organoid comprises epithelial cells.

In another embodiment, the invention provides an in vitro kidney organoid derived from primary kidney cancer tissue, wherein the organoid comprises epithelial cells.

In another embodiment, the invention provides a cell culture medium supplemented with fetal bovine serum (FBS).

In another embodiment, the invention provides a cell culture medium supplemented with FBS, basic fibroblast growth factor (bFGF), epidermal growth factor (EGF), and hydrocortisone.

In another embodiment, the invention provides a cell culture medium additionally supplemented with Insulin, Insulin Growth Factor 1 (IGF-1), Ascorbic acid, Heparin and Vascular endothelial growth factor (VEGF). To this medium, GSK3 inhibitor CH199022 and/or B27 supplement can be added. B27 supplement is commercially available from Gibco™ (order. No. 17504044) as B-27™ Supplement, Serum Free, 10 mL (used in the support of low or high density growth and short or long-term viability of hippocampal and CNS neurons, Gibco™ B27™ Supplement, Serum Free).

In another embodiment, the present invention provides a kit including a cell culture medium supplemented with FBS, and a cell culture medium supplemented with FBS, bFGF, EGF, and hydrocortisone.

In another embodiment, the invention provides a method for identifying agents having anticancer activity against kidney cancer cells including selecting at least one test agent, contacting a plurality of patient-specific kidney organoids derived from the patient's kidney cancer cell with the test agent, determining the number of kidney organoids in the presence of the test agent and the absence of the test agent, and identifying an agent having anticancer activity if the number or the growth of the organoid cells is less in the presence of the agent than in the absence of the agent. In another embodiment, the method provides a step of treating the patient with the agent identified as having anticancer activity against the patient-specific organoids but not against normal organoids. A method for identifying agents having anticancer activity against kidney cancer cells can further include providing a mouse engrafted with kidney cancer cells from the patient and containing a tumor formed from the kidney cancer cells; administering the identified agent having anticancer activity to the mouse; and determining if the tumor size is reduced in the presence of the identified agent. In another embodiment, a method for identifying agents having anticancer activity against kidney cancer cells can further include providing a humanized mouse engrafted with components of a patient's immune system and kidney cancer cells from the patient and containing a tumor formed from the kidney cancer cells; administering the identified agent to the humanized mouse; and comparing the size of the tumor in the humanized mouse with components of a patient's immune system to the size of the tumor in the mouse in which the identified agent was administered; and determining if the size of the tumor in the humanized mouse with components of a patient's immune system is reduced relative to the size of the tumor in the mouse in which the identified agent was administered. This and other embodiments can further include providing a humanized mouse engrafted with kidney cancer cells from the patient and containing a tumor formed from the kidney cancer cells; administering a control agent to the humanized mouse engrafted with kidney cancer cells from the patient; and comparing the size of the tumor in the humanized mouse engrafted with kidney cancer cells from the patient to the size of the tumor in the mouse in which the identified agent was administered; and determining if the size of the tumor in the mouse in which the identified agent was administered is reduced relative to the size of the tumor in the humanized mouse engrafted with kidney cancer cells from the patient.

In another embodiment, the invention provides a method for identifying agents having regenerative activity against kidney cells including selecting at least one test agent, contacting a plurality of patient-specific kidney organoids derived from the patient's kidney cell with the test agent, determining the number of kidney organoids in the presence of the test agent and the absence of the test agent, and identifying an agent having regenerative activity if the number or the growth of the organoid cells is more in the presence of the agent than in the absence of the agent.

In another embodiment, the method provides a step of treating the patient with the agent identified as having anticancer activity against the patient-specific organoids but not against normal organoids.

In another embodiment, the present invention provides normal patient-specific kidney organoids, and methods of using such organoids for personalized therapies for kidney cancer.

In another embodiment, the present invention provides immune humanized mice with implanted patient-specific kidney organoids, and methods of using such mice to identify personalized therapies for kidney cancer and other kidney disorders.

In the methods described herein, the organoids exhibit endogenous three-dimensional organ architecture.

DETAILED DESCRIPTION OF THE INVENTION

In certain embodiments, the present invention provides kidney organoids derived in vitro from normal and cancerous tissues, and methods of making and using such organoids, as well as cell culture media and kits. As disclosed in one embodiment herein, certain growth factors in an in vitro environment containing extracellular matrix molecules in a 3-dimensional culture device may be used to make the organoids.

An organoid is a miniature form of a tissue that is generated in vitro and exhibits endogenous three-dimensional organ architecture. See, e.g., Cantrell and Kuo (2015) *Genome Medicine* 7:32-34. The organoids of the present invention can be used, for example, to: a) determine genomic targets within tumors and prediction of response to therapies in preclinical and clinical trials; b) detect the activity of an anti-cancer agent by examining the number of surviving organoids after treatment; c) detect the activity of a proliferative agent by determining the number of proliferating cells within each organoid and determining gene expression profiling of relevant pathways; d) detect the activity of a renal regenerative agent by examining the number of organoids after treatment to regenerate the nephron and tubular structures of the kidney; e) examine the specificity of agents targeting different renal cell types within organoids; f) examine the toxicity of agents targeting renal tubular cell types within organoids; g) determine the effects of chemotherapy and radiation; h) create mouse models by implantation of the organoid in vivo; i) create preclinical models for examining therapy responses and drug discovery both in vitro and in vivo; and j) determine clonally-targeting anti-cancer therapies.

Accordingly, in one embodiment, the invention provides a method of making an organoid from a mammalian kidney tissue in vitro including: isolating cells from a mammalian kidney tissue to provide isolated cells; culturing the isolated cells in a differentiation medium for a time sufficient to enrich for stem cells and induce differentiation; and amplifying one or more of the cells by culturing in an extracellular matrix in an organoid medium for a time sufficient to produce organoids. One of ordinary skill in the art can determine a time sufficient to induce differentiation by examining morphological changes associated with differentiation. In one preferred embodiment, the time sufficient to induce differentiation is from about 3 to about 14 days. In another preferred embodiment, the time sufficient to induce differentiation is about 7 days. One of ordinary skill in the art can determine a time sufficient to induce organoid formation by examining morphological changes associated with organoid formation. In one preferred embodiment, the time sufficient to induce organoid formation is from about 5 to about 21 days. In another preferred embodiment, the time sufficient to induce organoid formation is about 14 days. In one embodiment, the isolated cells are epithelial cells. In one embodiment, a single kidney epithelial cell is amplified.

In one preferred embodiment, the differentiation medium comprises Endothelial Growth Medium EGM-2 (EGM-2) or advanced-Dulbecco's Modified Eagle Medium (ADMEM) and FBS. EGM-2 or ADMEM is typically used at 1×. The concentration of FBS present in the differentiation medium may range from about 1% to about 5%. In a further embodiment, the differentiation medium comprises one or both of Penicillin (500-5000 Units/mL) and Streptomycin (50-500 µg/mL). In a most preferred embodiment, the differentiation medium comprises the following concentrations: EGM-2 (Lonza) or ADMEM (ThermoFisher Scientific) (about 1×); FBS (about 2%); Penicillin (about 1000 Units/mL); and Streptomycin (about 100 µg/mL). The differentiation medium may further comprise or be substituted with other supplements, growth factors, antibiotics, vitamins metabolites, and hormones, synthetic or natural with similar properties as known in the art.

In one preferred embodiment, the organoid medium includes EGM-2 or ADMEM, FBS, bFGF, EGF, and hydrocortisone. The concentration of FBS present in the culture medium may range from about 1-5%). The concentration of bFGF present in the culture medium may range from about 0.1-100 mg/mL (e.g., 1 mg/mL, 5 mg/mL, 10 mg/mL, 15 mg/mL, 20 mg/mL, etc.). The concentration of EGF present in the culture medium may range from about 0.1-100 mg/mL (e.g., 1 mg/mL, 5 mg/mL, 10 mg/mL, 15 mg/mL, 20 mg/mL, 25 mg/mL, etc.). The concentration of hydrocortisone present in the culture medium may range from about 0.1-10 mM (e.g., 0.1 mM, 0.5 mM, 0.75 mM, 1 mM, 1.5 mM, 2 mM, 5 mM, etc.). In a preferred embodiment, the organoid medium further comprises Insulin and IGF-1. The concentration of Insulin present in the culture medium may range from about 1-100 mg/mL (e.g., 1 mg/mL, 5 mg/mL, 10 mg/mL, 15 mg/mL, 20 mg/mL, 49 mg/mL, 50 mg/mL, 51 mg/mL, 100 mg/mL, etc.). The concentration of IGF-1 present in the culture medium may range from about 1.0-200 ng/mL (1.0 ng/mL, 10 ng/mL, 50 ng/mL, 75 ng/mL, 100 ng/mL, 125 ng/mL, 150 ng/mL, 175 ng/mL, 200 ng/mL, etc.). In a further embodiment, the organoid medium further includes one or more of the following: Ascorbic Acid (about 1-100 µg/mL, e.g., 1 µg/mL, 5 µg/mL, 10 µg/mL, 15 µg/mL, 20 µg/mL, 49 µg/mL, 50 µg/mL, 51 µg/mL, 100 µg/mL, 125 µg/mL etc.), Heparin (about 0.1-100 µg/mL, e.g., 1 µg/mL, 5 µg/mL, 10 µg/mL, 15 µg/mL, 20 µg/mL, etc.), VEGF (about 0.1-100 ng/mL, e.g., 1 ng/mL, 5 ng/mL, 10 ng/mL, 15 ng/mL, 20 ng/mL, 25 ng/mL, etc.), Penicillin (about 500-5000 Units/mL), and Streptomycin (about 50-500 µg/mL).

In one preferred embodiment, the organoid medium includes B27 supplement (about 0.1-100 µl/mL, e.g., 1 µl/mL, 5 µl/mL, 10 µl/mL, 15 µl/mL, 20 µl/mL, 25 µl/mL, etc.), and GSK3 inhibitor CHIR99021 (about 0.1-10 µM, e.g., 0.1 µM, 0.5 µM, 0.75 µM, 1 µM, 1.5 µM, 2 µM, 5 µM, etc.). In a most preferred embodiment, the organoid medium includes the following concentrations: EGM-2 or ADMEM at 1×, approximately 2% FBS, approximately 10 mg/mL bFGF, approximately 20 mg/mL EGF, approximately 1 mM hydrocortisone, approximately 50 mg/mL Insulin, approximately 100 ng/mL IGF-1, approximately 50 µg/mL Ascorbic acid, approximately 10 µg/mL Heparin, approximately 20 ng/mL VEGF, approximately 1000 Units/mL Penicillin, approximately 100 m/mL Streptomycin, approximately 20 µl/mL B27 supplement, and approximately 1 µM CHIR99021. The organoid medium may further include or be substituted with other supplements, growth factors, antibiotics, vitamins metabolites, and hormones, synthetic or natural with similar properties as known in the art.

In certain embodiments, the cells are from human kidney tissue, and human primary kidney cancer tissue. In certain embodiments, cells that may be used to make an organoid are human kidney stem-like cells. Such cells are known in the art and may be identified and isolated using markers, for example, PAX2, PAX8, RCC marker, CD10, GATA3, paralbumin, claudins, S100A, cytokeratin 18 (CK18) and vimentin.

In one embodiment, the cells are positive for at least one marker selected from the group consisting of CK18, vimentin, PAX8, and GATA3. In another embodiment, the cells are positive for CK18, vimentin, PAX8, and GATA3. Such cells may be identified and isolated by methods of cell sorting that are known in the art. For example, in one embodiment, the cells may be isolated by laser capture microdissection or RNA sorting using methods known in the art, such as molecular beacons and the SmartFlare™ probe protocol (EMD Millipore).

In one preferred embodiment, the cells are obtained from surgically excised tissues by subjecting the tissues to mechanical dissociation, collagenase treatment, and filtration.

In certain embodiments the method is performed with a commercially available extracellular matrix such as Matrigel™. Other natural or synthetic extracellular matrices are known in the art for culturing cells. In general, an extracellular matrix comprises laminin, entactin, and collagen. In a preferred embodiment the method is performed using a 3-dimensional culture device (chamber) that mimics an in vivo environment for the culturing of the cells, where preferably the extracellular matrix is formed inside a plate that is capable of inducing the proliferation of stem cells under hypoxic conditions. Such 3-dimensional devices are known in the art. An example of such a device is disclosed by Bansal, N., et al. (2014) Prostate 74, 187-200, the disclosure of which is incorporated herein by reference in its entirety. It has been discovered in accordance with the present invention that the use of a 3-dimensional culture device in a method of making organoids has surprising advantages over other formats, as shown in Table 1.

TABLE 1

Advantages and disadvantages of tested formats

| Format | Consistency of Organoids | Reproducibility | Efficiency |
|---|---|---|---|
| In Matrigel ™ | +++ | +++ | ++++ |
| On Matrigel ™ | + | --- | ++ |
| Hanging Drop plates | --- | --- | --- |
| Non adherent plate | + | --- | + |

In another aspect, the invention provides a kidney organoid. Normal human kidney tissue includes collecting duct and nephrons. The kidney organoids of the present invention resemble the structures of the primary tissue. Upon histological and immunofluorescence analyses, one of skill in the art can determine that the organoids recreate the human tubules, collecting duct and nephrons. Kidney tissue origin of organoids can be confirmed by detecting the expression of CK18, vimentin, PAX8 and GATA3.

In another aspect, the invention provides a kidney organoid derived in vitro from primary kidney cancer tissue. Tumor heterogeneity can be efficiently modeled using the methods described to make an organoid, by mapping the diagnostic dominant clone and tumor subclones from each patient biopsy sample, generating organoids derived from each clone and defining the genetic signature of each clone. A kidney organoid derived from primary kidney cancer tissue will generally maintain expression of kidney lineage-specific markers and the functional excretory profile of the original primary tissue. A kidney organoid as described herein can be serially propagated, cryofrozen and regenerated and established as a model for cancer drug discovery and precision therapy.

In another aspect, the invention provides a kidney organoid derived in vitro from surgically excised tissues of tumors identified to express histopathological tissue specific and tumorigenic markers. Single cells from these tissues may be isolated with non-contact laser capture microdissection, with cell sorting or by RNA sorting, for example using SmartFlare™ probes to generate single cell organoids with known expression features.

The organoids described herein exhibit endogenous three-dimensional organ architecture.

In another embodiment, the invention provides a method for identifying agents having anticancer activity against kidney cancer cells from a patient(s) including selecting at least one test agent, contacting a plurality of patient-specific kidney organoids derived from the patient's kidney cancer cell with the test agent, determining the number of kidney organoids in the presence of the test agent and the absence of the test agent, and identifying an agent having anticancer activity if the number or growth of the organoids is less in the presence of the agent than in the absence of the agent. In another embodiment, the method provides a step of treating the patient with the agent identified as having anticancer activity against the patient-specific organoids. A method for identifying agents having anticancer activity can further include providing a mouse engrafted with kidney cancer cells from the patient and containing a tumor formed from the kidney cancer cells; administering the identified agent having anticancer activity to the mouse; and determining if the tumor size is reduced in the presence of the identified agent.

A method for identifying agents having anticancer activity can further include providing a humanized mouse engrafted with components of a patient's immune system and kidney cancer cells from the patient and containing a tumor formed from the kidney cancer cells; administering the identified agent to the humanized mouse; and comparing the size of the tumor in the humanized mouse with components of a patient's immune system to the size of the tumor in the mouse in which the identified agent was administered; and determining if the size of the tumor in the humanized mouse with components of a patient's immune system is reduced relative to the size of the tumor in the mouse in which the identified agent was administered. In this embodiment, the humanized mice with the patient's immune system can be used to compare the effects of the identified agent (e.g., candidate therapeutic) on tumors in the presence or absence of immune cells to examine a potential role for combination with immunotherapy. These methods can further include providing a humanized mouse (an immune-deficient control mouse) engrafted with kidney cancer cells from the patient and containing a tumor formed from the kidney cancer cells; administering a control agent to the humanized mouse engrafted with kidney cancer cells from the patient; and comparing the size of the tumor in the humanized mouse engrafted with kidney cancer cells from the patient to the size of the tumor in the mouse in which the identified agent was administered; and determining if the size of the tumor in the mouse in which the identified agent was administered is reduced relative to the size of the tumor in the humanized mouse engrafted with kidney cancer cells from the patient. In this method, if the size of the tumor in the mouse in which the identified agent was administered is reduced relative to the size of the tumor in the humanized mouse engrafted with kidney cancer cells from the patient, the identified agent can be confirmed as a successful treatment for cancer in the patient.

In another embodiment, the invention provides a method for identifying agents having regenerative activity against kidney cells including selecting at least one test agent, contacting a plurality of patient-specific kidney organoids derived from the patient's kidney cell with the test agent, determining the number of kidney organoids in the presence of the test agent and the absence of the test agent, and identifying an agent having regenerative activity if the number or growth of the organoids is more in the presence of the agent than in the absence of the agent. In another embodiment, the method provides a step of treating the renal failure patient with the agent identified as having regenerative activity against the patient-specific organoids.

In another embodiment, the invention provides a method of selecting a personalized treatment for kidney cancer in a subject including: selecting at least one form of treatment, contacting a plurality of kidney organoids with the form of treatment, wherein the organoids are derived from kidney cancer cells from the subject, determining the number of kidney organoids in the presence of the treatment and the absence of the treatment, and selecting the treatment if the number or growth of the kidney organoids is less in the presence of the treatment than in the absence of the treatment. Various types of therapy can then be examined using the organoids to determine therapy resistance before initiation, to tailor the therapy for each individual patient based on oncogenic driver expression in the organoids, as well as further study induced clonal selection processes that are the frequent causes of relapse. Various forms, combinations, and types of treatment are known in the art, such as radiation, hormone, chemotherapy, biologic, and bisphosphonate therapy. The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject. Terms such as "treating" or "treatment" or "to treat" or "alleviating" or "to alleviate" refer to therapeutic measures that cure, slow down, lessen symptoms of, and/or halt progression of a diagnosed pathologic condition.

The foregoing methods may be facilitated by comparing therapeutic effects in organoids derived from cancer cells and normal cells from the same patient. For example, normal organoids and cancer organoids derived from cells of the same patient can be assessed to determine genetic and epigenetic mutations and gene expression profiles that are cancer-specific, thereby allowing the determination of gene-drug associations and optimization of treatment. Such comparisons also allow one to predict a therapeutic response and to personalize treatment in a specific patient.

In another aspect of this method, clonally targeted therapies can be determined by testing the effect of a therapeutic agent on multiple organoids derived from subsequently determined dominant clones of kidney cancer cells identified in the tumor tissue from a patient, and comparing to the effect of the therapeutic agent on organoids derived from normal cells of the same patient.

In another aspect, the invention provides a cell culture (e.g., organoid) medium supplemented with FBS, bFGF, EGF and hydrocortisone. In another embodiment, the invention provides a cell culture (e.g., organoid) medium supplemented with FBS, bFGF, EGF, hydrocortisone, Insulin, IGF-1, Ascorbic acid, Heparin, and VEGF. In another embodiment, the invention provides a cell culture (e.g., organoid) medium supplemented with FBS, bFGF, EGF, hydrocortisone, Insulin, IGF-1, Ascorbic acid, Heparin, VEGF, B27 supplement, and CHIR99021. In another embodiment, the invention provides a cell culture (e.g., organoid) medium supplemented with FBS, bFGF, EGF, hydrocortisone, Insulin, IGF-1, Ascorbic acid, Heparin, VEGF, Penicillin and Streptomycin. In another embodiment, the invention provides a cell culture (e.g., organoid) medium supplemented with FBS, bFGF, EGF, hydrocortisone, Insulin, IGF-1, Ascorbic acid, Heparin, VEGF, B27 supplement, CHIR99021, Penicillin and Streptomycin. In a preferred embodiment, the medium is a commercially available cell growth medium such as EGM-2 (Lonza) or ADMEM (ThermoFisher scientific).

In another aspect, the invention provides kits to make an organoid from a single cell. In an embodiment, a kit contains containers for a differentiation medium and an organoid medium as previously described. The containers may also contain the necessary supplements (growth factors, antibiotics, hormones, vitamins, amino acids, and combinations thereof) for a differentiation medium and an organoid medium. The kit may further include the necessary components for a 3-dimensional culture device, for example, plates, and/or materials for an extracellular matrix, e.g. Matrigel™. The kit may further contain a set of instructions to perform the methods of making an organoid from a single cell as previously described.

In another embodiment, the present invention provides a mouse with an implanted patient-specific kidney organoid. In one embodiment, the mouse is a humanized mouse. In another embodiment, the mouse is a human immune system (HIS)—reconstituted mouse. In another embodiment, the mouse is non-obese diabetic (NOD)-Rag (−)-γ chain (−) (NRG) mouse. In another embodiment, the mouse is an NSG immune-deficient PDX mouse.

Methods of making HIS-reconstituted mice are known in the art and disclosed for example by Drake et al. (2012) *Cell Mol Immunol* 9:215-24 and Harris et al. (2013) *Clinical and Experimental Immunology* 174:402-413. In accordance with one aspect of the present invention, human stem cells from patient, for example from a diagnostic bone marrow or blood sample or HLA-matched, are transplanted into neonatal NRG mice to engraft components of the patient's immune system. Methods of making NSG immune-deficient PDX mice are also known in the art and disclosed for example by Thong et al. (2014) *Urol Oncol* 43:e23-30. The mice are later subjected to grafting with kidney organoids derived from kidney cells of the same patient orthotopically in the mouse under the renal capsule. The mice are useful for identifying new treatments, assessing responses to therapy, and evaluating combination therapies.

The following non-limiting examples serve to further illustrate the invention.

Example 1

Organoids from both kidney cancer and kidney normal adjacent tissue (NAT) were generated, with the latter being valuable in use for kidney failure and organ replacement therapy, as a part of an overall regenerative medicine indication(s). The organoids tissue generated using the methods described herein are all adult-tissue derived, patient-derived, organ-derived and generated in 3D culture defined conditions. The robust 3D culture system described herein enables the stable long-term in vitro propagation of human nephron progenitors. Long-term cultured nephron progenitors can be harnessed for rapid and efficient generation of nephron organoids, thereby providing an accessible system for modeling kidney development, renal toxicity testing, gene editing, and disease modeling. Table 2 below includes the media and culture conditions in a typical embodiment of producing kidney tissue organoids.

TABLE 2

Kidney Organoid Media

| Primary Tissue | Collection Media | Process Time | 2D Culture (phase I) | 3D Culture (Phase II in Matrigel) | Days to organ- oids |
|---|---|---|---|---|---|
| Kidney | DMEM medium + 10% FBS Penicillin (3,000 Units/mL) + Streptomycin (300 µg/mL) | Dissoci- ate tissue for only 0.5-2 hours | EGM-2 or ADMEM medium + 2% FBS + Penicillin (1,000 Units/mL) + Streptomycin (100 µg/mL) | EGM-2 or ADMEM medium + 2% FBS bFGF (10 mg/ml) + EGF (20 mg/mL) + (Hydro- cortisone | Phase I: 7 Phase II: 14 |

TABLE 2-continued

Kidney Organoid Media

| Primary Tissue | Collection Media | Process Time | 2D Culture (phase I) | 3D Culture (Phase II in Matrigel) | Days to organ- oids |
|---|---|---|---|---|---|
| | | | | 1 mM) + Insulin (50 mg/ml) + IGF-1 (100 ng/mL) + Ascorbic acid (50 µg/mL) + Heparin (10 µg/mL) + VEGF (20 ng/mL) + Penicillin (1,000 Units/mL) + Streptomycin (100 µg/mL) Adding B27 (20 µl/mL), 12 h pulse CHIR99021 (1 µM) induce differentiation | |

Example 2

Sixteen patient-derived kidney tissues were collected. From twelve of these patients, both tumor and normal tissues were collected, and tumor only was collected from 4 patients. More than 90% of the renal cell carcinoma (RCC) arise from the renal tubules. RCC is divided into 5 main histologic subtypes: clear cell, papillary, chromophobe, collecting duct, and unclassified RCC. Clear cell, papillary, and chromophobe RCCs are the 3 most common types, comprising 70% to 80%, 14% to 17%, and 4% to 8% of all RCCs, respectively. Collecting duct carcinoma is the rarest type of RCC (1%). Unclassified RCCs include those that do not fit into any of the above 4 subtypes either morphologically or cytogenetically. In a healthy kidney, each nephron segment possesses a distinct and specific immunoprofile. Each major type of renal epithelial neoplasm is thought to be derived from a specific nephron segment, and thus, is expected to display an immunoprofile akin to that of the parental nephron segment, for examples, the RCC marker and CD10 for proximal tubules and the corresponding clear cell and papillary RCCs; parvalbumin, S100A, claudins, kidney-specific cadherin for distal portion of the nephron, and the corresponding chromophobe RCC and oncocytoma; and high-molecular-weight cytokeratins for the collecting duct and the corresponding collecting duct RCC. All major types of renal tumors express CK18, whereas CK20 is negative in all of them. Vimentin, a broad mesenchymal marker, is expressed by most types of RCC, often in a diffuse fashion. Among the primary renal neoplasms, a differential immunoreactivity may facilitate tumor typing because vimentin is expressed in most (87%-100%) clear cell and papillary RCCs but only rarely in chromophobe RCC and oncocytoma. The available data suggest the panel for evaluating RCC should include PAX2 or PAX8 and the RCC marker or CD10. The expression of these markers was detected in the 3D organoids.

Example 3

The human kidney contains up to 2 million epithelial nephrons responsible for blood filtration. Regenerating the kidney requires the induction of the more than 20 distinct cell types required for excretion and the regulation of pH, and electrolyte and fluid balance. Herein is described the induction of progenitors for both collecting duct and nephrons via the directed differentiation of patient-derived normal and RCC cells derived from nephrectomy tissues. Under an IRB-approved protocol, nephrectomy specimens from high-risk RCC cases were collected and processed within 15 minutes of surgery. Areas containing tumor as deemed by the pathologist and normal adjacent tissue counterpart were microdissected. A 3D culture system fit for growth of kidney cells was first developed by isolating epithelial cells microdissected from primary RCC specimens. Qualified pathologists confirmed their renal origin from the corresponding H&E. Nephrectomy-derived normal adjacent tissue (NAT) and RCC cells were utilized to determine best conditions for generating organoids. A two-step methodology comprising a first phase of adult kidney stem cell enrichment, conducted in a 2D setting (stage I), followed by a second phase of organoid 3D growth obtained in pure matrigel chambers (stage II), was conducted. For 2D stage I culture, the optimum media to use of either EGM2 or ADMEM that allowed growth of organoids in stage II from single cells within 14 days was identified. Stage I media included using either EGM2 or ADMED complete medium (with the addition of EGF, BFGF, IGF-1, VEGF, hydrocortisone, ascorbic acid, insulin, heparin, gentamicin, amphotericin-B, and 2% FBS). It was found that the organoid forming efficiency (OFE) was improved by the addition of IGF-1, Insulin and VEGF to the culture media components.

Cells were placed in 3D droplet culture chambers in stage II complete media containing Matrigel, to mimic the basal lamina of the normal renal tissue, and growth factors in conditions that permits cellular self-organization of organoid forming cells. Kidney cells were embedded as single cells in 3D-well plates. Organoid formation was then followed microscopically daily for 2 weeks. The success rate in making 3D organoids from renal tissues was 100% from normal kidney tissue and 83% from RCC. To further demonstrate that the clonally proficient adult-tissue derived single cells can generate differentiated kidney cells, the organoids were evaluated for kidney specific markers, including assessing the kidney epithelium lineage-specific marker luminal CK18, vimentin and kidney specific PAX8 and GATA3. The kidney tissue origin of organoids was confirmed by detecting the expression of PAX8.

When a nephrectomy tissue from a patient with clear cell RCC was utilized, organoids formed in 3D culture appeared with a phenotype associated with clear cells. Normal kidney organoids showed potentially nephron-derived organoids as suggested by bright field images and corresponding H&E staining of these organoids upon embedding in paraffin. It was found that the kidney OFE improved by the addition of IGF-1, VEGF, heparin and Insulin to the culture media. However, the effects of addition of IGF-1 were not dose-dependent since doubling the IGF-1 dose (2×) in culture did not increase the OFE.

The organoids generated from multiple patient samples had various phenotypes during the different times of 2D culture. A similar diversity in phenotypes was also detected in the 3D culture stage. Moreover, the organoids formed in 3D culture had both spherical or branching shapes. When CHI99022 (1 µM) was added to the media as a pulse for 12 h then media was replaced with fresh media without CHIR, branching tubular shaped organoids increased. In another group of experiments, the effects of addition of 1× B27 supplement were examined. The addition of 1×B27 supplement slightly but not significantly increased RCC but not normal kidney organoid numbers.

The Wnt signaling pathway is known to trigger the initiation of nephron progenitor cell differentiation. The effects of activating Wnt signaling in organoid studies was examined. Cultured 2D and 3D cells were treated with a GSK3 inhibitor CHIR99021 (CHIR), which activates the canonical Wnt signaling pathway. CHIR99021 treatment led to induced differentiation in cultured nephron progenitor cells accompanied by cell death, leading to smaller size organoids. On the other hand, branching tubular shaped organoids increased. These studies suggest that Wnt signaling activation is important for tubular but not nephron organoid formation.

Organoids grown in 3D matrix (matrigel) culture expressed the kidney marker vimentin, and the epithelial cell markers CK8/18. The 3D formed cells showed vimentin expression, further validating the hypothesis that 3D organoid culture enriches for kidney features. The presence of matrix is essential to maintain these expression features since 3D liquid cultures had different expression profiles. To further assess the optimum conditions for 3D culture, the addition of 1×B27 (−Vitamin A) (1×, Gibco, #12587001) supplement was examined. Addition of the B27 supplement resulted in a change in 3D culture cell phenotype with reduction in CK8/18 and much more reduction in vimentin expression. Collectively, these data indicate that adult-tissue patient-derived organoids (PODs) were generated from normal kidney tissues and RCC, and that organoids contain cellular expression of kidney-specific cell subtypes. These kidney organoids represent powerful models of the human organ for future applications, including renal regeneration, nephrotoxicity screening, disease modelling and as a source of cells for personalized therapy for not only RCC but also other renal disorders.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein by reference in their entireties.

I claim:

1. A method of making an organoid from a mammalian kidney tissue in vitro comprising: isolating cells from a mammalian kidney tissue to provide isolated cells; culturing the isolated cells for a time sufficient to enrich for stem cells; and amplifying one or more of the stem cells by culturing in an extracellular matrix in an organoid medium for a time sufficient to produce organoids that are each clonally derived from a single stem cell and exhibit endogenous three-dimensional organ architecture, wherein the organoid medium comprises FBS, basic fibroblast growth factor (bFGF), epidermal growth factor (EGF), hydrocortisone, Insulin, Insulin Growth Factor 1 (IGF-1), Ascorbic acid, Heparin, VEGF, Penicillin, Streptomycin, B27 supplement, and a GSK3 inhibitor.

2. The method of claim 1 wherein the mammalian kidney tissue is a human kidney tissue.

3. The method of claim 2, wherein the human kidney tissue is primary human normal kidney tissue, or primary human kidney cancer tissue.

4. The method of claim 1 wherein the organoids comprise epithelial cells.

5. The method of claim 1 wherein the time sufficient produce organoids is about fourteen days.

6. The method of claim 1 wherein the FBS is present at a concentration of about 1-5%, the bFGF is present at a concentration of about 1-50 mg/mL, the EGF is present at a concentration of about 1-50 mg/mL, and the hydrocortisone is present at a concentration of about 0.1-10 mM.

7. The method of claim 1 wherein the FBS is present at a concentration of about 2%, the bFGF is present at a concentration of about 10 mg/mL, the EGF is present at a concentration of about 20 mg/mL, and the hydrocortisone is present at a concentration of about 1 mM.

8. The method of claim 1 wherein the organoid medium comprises Insulin at a concentration of about 50 mg/mL, IGF-1 at a concentration of about 100 ng/mL, Ascorbic acid at a concentration of about 50 μg/mL, Heparin at a concentration of about 10 μg/EGF at a concentration of about 20 ng/mL, Penicillin at a concentration of about 1000 Units/mL, Streptomycin at a concentration of about 100 μg/mL, B27 supplement at a concentration of about 20 μl/mL, and CHIR99021 at a concentration of about 1 μM.

9. The method of claim 1 wherein the isolated cells are positive for at least one marker selected from the group consisting of luminal cytokeratin 18 (CK18), vimentin, PAX8 and GATA3.

\* \* \* \* \*